United States Patent
Norris et al.

(10) Patent No.: US 8,551,143 B2
(45) Date of Patent: Oct. 8, 2013

(54) LOW PROFILE PERIARTICULAR TENSION BAND PLATING SYSTEM WITH SOFT TISSUE NEUTRALIZATION CABLE TUNNEL/CHANNEL

(76) Inventors: Brent Lane Norris, Tulsa, OK (US);
Paul Ryan Stafford, Tulsa, OK (US);
Dana James Funk, Tulsa, OK (US)

(*) Notice: Subject to any disclaimer, the term of this patent is extended or adjusted under 35 U.S.C. 154(b) by 80 days.

(21) Appl. No.: 13/270,870

(22) Filed: Oct. 11, 2011

(65) Prior Publication Data
US 2013/0090694 A1 Apr. 11, 2013

(51) Int. Cl.
*A61B 17/80* (2006.01)
(52) U.S. Cl.
USPC .............................. 606/280; 606/284; 606/286
(58) Field of Classification Search
USPC ........... 606/74, 280, 281, 283, 284, 285, 286, 606/902, 905, 906
See application file for complete search history.

(56) References Cited

U.S. PATENT DOCUMENTS

| | | | |
|---|---|---|---|
| 3,824,995 A | 7/1974 | Getscher et al. | |
| 4,896,668 A * | 1/1990 | Popoff et al. | 606/74 |
| 5,797,916 A | 8/1998 | McDowell | |
| 6,066,141 A | 5/2000 | Dall et al. | |
| 6,093,201 A | 7/2000 | Cooper et al. | |
| 6,235,033 B1 | 5/2001 | Brace et al. | |
| 6,338,734 B1 | 1/2002 | Burke et al. | |
| 6,827,574 B2 | 12/2004 | Payton | |
| 7,207,993 B1 | 4/2007 | Baldwin et al. | |
| 7,229,444 B2 | 6/2007 | Boyd | |
| 7,611,513 B2 | 11/2009 | Deloge et al. | |
| 2006/0058795 A1 | 3/2006 | Boyd | |
| 2006/0058796 A1 | 3/2006 | Hartdegen et al. | |
| 2006/0229620 A1 | 10/2006 | Rothman et al. | |
| 2006/0235401 A1 | 10/2006 | Baldwin et al. | |
| 2008/0234679 A1 | 9/2008 | Sarin et al. | |
| 2009/0012569 A1 | 1/2009 | Dall et al. | |
| 2009/0105717 A1 | 4/2009 | Bluechel | |
| 2009/0287258 A1 | 11/2009 | Vannemreddy | |
| 2010/0094294 A1 | 4/2010 | Gillard et al. | |
| 2010/0137866 A1 | 6/2010 | Gelfand | |
| 2011/0029025 A1 | 2/2011 | Medoff | |

FOREIGN PATENT DOCUMENTS

CN 201135488 * 10/2008

OTHER PUBLICATIONS

Partial translation of CN 201135488 (human translation by Irina Knizhnik dated Feb. 22, 2013).*
Complete translation of CN 201135488 (machine translation from http://worldwide.espacenet.com/?locale=EN_ep dated Feb. 21, 2013).*

* cited by examiner

*Primary Examiner* — Kevin T Truong
*Assistant Examiner* — Christian Sevilla
(74) *Attorney, Agent, or Firm* — Head, Johnson & Kachigian, P.C.

(57) ABSTRACT

A bone plating system comprising: a plate, where the plate is low-profile and capable of contouring to a bone; a variable number of screw holes, locking or non-locking; at least one channel or tunnel through the plate; and at least one flexible device passing through the channel or tunnel and passing through soft tissue attached to the bone. The low profile plate, in combination with the flexible device passing through the surrounding soft tissue, functions as a tension band and acts to neutralize the muscle forces tending to pull the bone apart at a fracture. The low profile tension band plating system is targeted for periarticular tensile fractures for repair of patella, olecranon, greater trochanter, greater tuberosity, radial styloid, lateral or medial malleoli, or lateral malleolus.

7 Claims, 8 Drawing Sheets

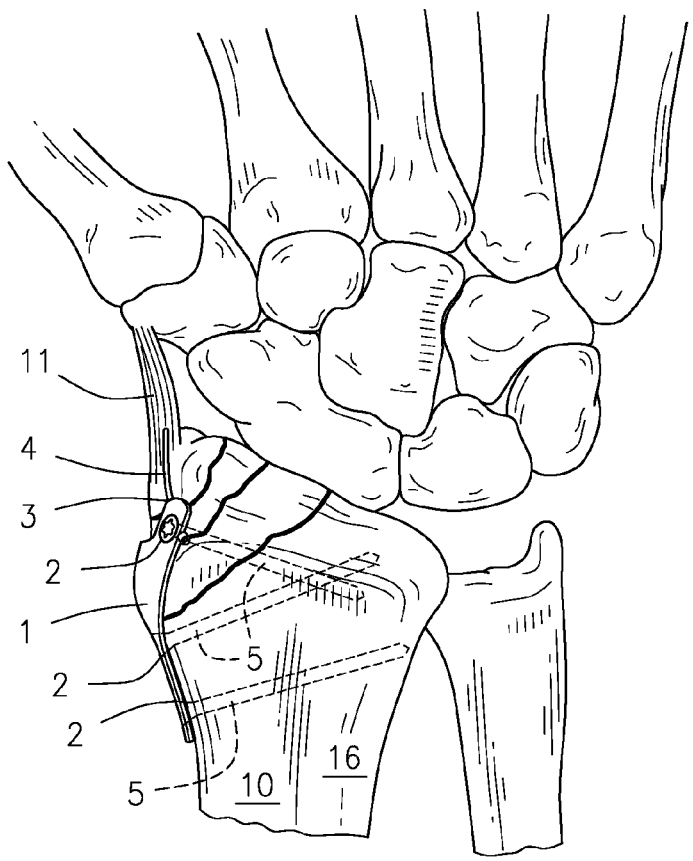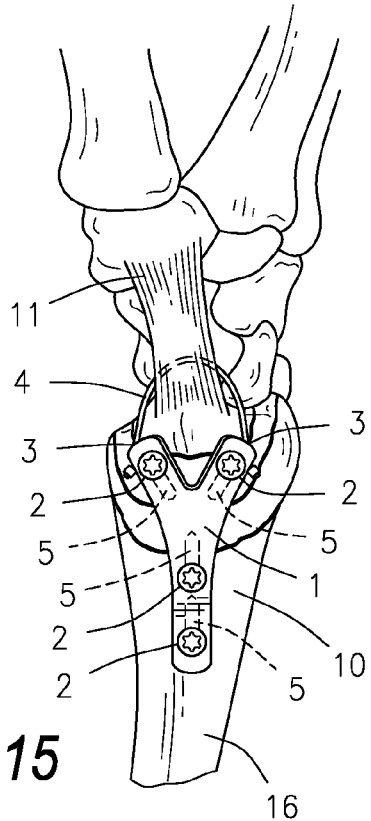
FIG. 14
FIG. 15

LOW PROFILE PERIARTICULAR TENSION BAND PLATING SYSTEM WITH SOFT TISSUE NEUTRALIZATION CABLE TUNNEL/CHANNEL

CROSS REFERENCE

Not Applicable.

BACKGROUND OF THE INVENTION

1. Field of the Invention

This invention relates generally to a fracture plating system, and more particularly, but not by way of limitation, to a low profile periarticular tension band plating system with soft tissue neutralization cable tunnel/channel.

2. Description of the Related Art

Small bone periarticular fractures, such as fractures around the knee and elbow, can be problematic because of limited soft tissue coverage and the small size of bone fragments. Fracture plates currently available to treat these simple tensile fractures are bulky and are often prominent, leading to a secondary surgery for hardware removal. Current plate systems require suitable bone quantity and quality and a fracture pattern compatible with the device.

Additionally, a figure eight tension band wire is often used for treatment of simple fractures around knee and elbow. Such wire is difficult to place, remains prominent, and applies a variable and unknown amount of tension.

Another example of traditional cable fixation encircles the bone and induces a variable but often large amount of soft tissue trauma, potentially devitalizing the surrounding bone.

Based on the foregoing, it is desirable to provide a low profile fracture plating system with cable fixation that can be passed easily into the surrounding soft tissues.

It is further desirable to provide such a system that is made specifically for simple tensile fracture patterns and small bone fragments.

It is further desirable to provide such a system that functions as a tension band.

It is further desirable to provide such a system that does not encircle the bone, resulting in less soft tissue damage and therefore less bone devitalization.

It is further desirable to provide such a system that allows the reduction clamp to stay in place during placement of the plating system.

SUMMARY OF THE INVENTION

In general, in a first aspect, the invention relates to a bone plating system comprising: a plate, where the plate is low-profile and capable of contouring to a bone; at least one channel or tunnel through the plate; and at least one flexible device passing through the channel or tunnel and passing through soft tissue attached to the bone. The at least one flexible device may be capable of neutralizing tensile forces, and may not surround the bone, except occasionally when circumferential wiring is used around the patella. The plate may be capable of being contoured to the bone in situ. The bone plating system may further comprise one or more holes in the plate and one or more screws attaching the plate to the bone via the one or more holes. The one or more holes may be threaded and the one or more screws may be locking screws, non-locking screws, or a combination thereof. The at least one flexible device may be a cable, suture, wire, elastic device, or combination thereof. The soft tissue may be a tendon, ligament, or fascia.

When the bone is a patella with soft tissue extending upward from the patella and downward from the patella or encircling the patella, the plate may be generally X-shaped such that the plate has two arms extending generally upward and two arms extending generally downward. The at least one channel or tunnel may pass through each of the two arms extending generally upward from the plate and each of the two arms extending generally downward from the plate. The flexible device may pass through the channel or tunnel in each of the two arms extending generally upward and through the soft tissue extending upward from the patella, and a second flexible device may pass through the channel or tunnel in each of the two arms extending generally downward and through the soft tissue extending downward from the patella. Alternately, the flexible device may pass through the channel or tunnel in each of the two arms extending generally upward, through the channel or tunnel in each of the two arms extending generally downward, and through the soft tissue extending upward and downward from the patella.

When the bone is an olecranon with soft tissue extending upward from the olecranon, the plate may generally have an elongated X shape, such that the plate has a center section, two arms extending generally upward, and two arms extending generally downward. The at least one channel or tunnel may pass through each of the two arms extending generally upward from the plate. The flexible device may pass through the channel or tunnel in each of the two arms extending generally upward and through the soft tissue extending upward from the olecranon.

When the bone is a greater trochanter with soft tissue extending upward from the greater trochanter, the plate may be generally Y-shaped, such that the plate has a downward-extending arm and two arms extending generally upward. The at least one channel or tunnel may pass through each of the two arms extending generally upward from the plate. The flexible device may pass through the channel or tunnel in each of the two arms extending generally upward and through the soft tissue extending upward from the greater trochanter.

When the bone is a greater tuberosity with soft tissue extending upward from the greater tuberosity, the plate may be generally T-shaped, such that the plate has a downward-extending arm and an upper portion extending anterior and posterior on the humerus. The at least one channel or tunnel may pass through the upper portion of the plate. The flexible device may pass through the channel or tunnel in the upper portion of the plate and through the soft tissue extending upward from the greater tuberosity.

When the bone is a radial styloid with soft tissue extending upward from the radial styloid, the plate may be generally Y-shaped, such that the plate has a downward-extending arm and two arms extending generally upward. The at least one channel or tunnel may pass through each of the two arms extending generally upward from the plate. The flexible device may pass through the channel or tunnel in each of the two arms extending generally upward and through the soft tissue extending upward from the radial styloid.

When the bone is a medial malleoli with soft tissue extending downward from the medial malleoli, the plate may be generally shaped like an upside-down Y, such that the plate has an upward-extending arm and two arms extending generally downward. The at least one channel or tunnel may pass through each of the two arms extending generally downward from the plate. The flexible device may pass through the channel or tunnel in each of the two arms extending generally downward and through the soft tissue extending downward from the medial malleoli.

When the bone is a lateral malleolus with soft tissue extending downward from the fibula, the plate may be generally shaped like an upside-down Y, such that the plate has an upward-extending arm and two arms extending generally downward. The at least one channel or tunnel may pass through each of the two arms extending generally downward from the plate. The flexible device may pass through the channel or tunnel in each of the two arms extending generally downward and through the soft tissue extending downward from the fibula.

The bone plating system may be used according to the following method: clamping a broken bone; applying a plate to the bone, where the plate is low-profile and has at least one channel or tunnel therethrough; passing a flexible device through the at least one channel or tunnel and through soft tissue surrounding the bone; and unclamping the bone. The method may further comprise contouring the plate to the bone after applying the plate to the bone, and/or attaching the plate to the bone with one or more screws prior to passing the flexible device through the at least one channel or tunnel and through the soft tissue surrounding the bone. The at least one channel or tunnel may be at least one channel located adjacent to at least one hole through which the one or more screws attaches the plate to the bone and the one or more screws may each have a screw head; if so, the method may further comprise tightening the one or more screws after passing the flexible device through the at least one channel and through the soft tissue surrounding the bone, such that the flexible device is located in the at least one channel underneath the screw heads and the screw heads maintain the flexible device within the at least one channel. If the flexible device is wire, the method may further comprise crimping the wire to secure the wire to the plate by preventing the wire from unthreading from the at least one channel or tunnel. If the flexible device is a suture, the method may further comprise tying the suture to secure the suture to the plate by preventing the suture from unthreading from the at least one channel or tunnel. If the flexible device is cable, the method may further comprise crimping the cable to secure the cable to the plate by preventing the cable from unthreading from the at least one channel or tunnel. If the flexible device is an elastic polymer, the method may further comprise tying the elastic polymer to secure the elastic polymer to the plate by preventing the elastic polymer from unthreading from the at least one channel or tunnel.

BRIEF DESCRIPTION OF THE DRAWINGS

FIG. 14 is a side view of the bone plating system in place on a radial styloid;

FIG. 15 is a front view of the bone plating system in place on a radial styloid;

DETAILED DESCRIPTION OF THE INVENTION

The devices and methods discussed herein are merely illustrative of specific manners in which to make and use this invention and are not to be interpreted as limiting in scope.

While the devices and methods have been described with a certain degree of particularity, it is to be noted that many modifications may be made in the details of the construction and the arrangement of the devices and components without departing from the spirit and scope of this disclosure. It is understood that the devices and methods are not limited to the embodiments set forth herein for purposes of exemplification.

In general, in a first aspect, the invention relates to a semi-rigid bone plate that functions as a tension band, combined with soft tissue cabling, suturing, or other flexible device to augment and extend fixation. The device is best used for the surgical repair of simple tensile fractures that occur with relative frequency in specific anatomical regions of the body with minimal soft tissue coverage. In particular, the low profile tension band plating system is targeted for periarticular tensile fractures for repair of patella, olecranon, greater trochanter, greater tuberosity, radial styloid, lateral and medial malleoli, or lateral malleolus.

As shown in FIGS. 1 through 19, the system is comprised of a plate 1, which may be low profile and malleable such that it can be easily contoured to the surface of the bone 10. Such contouring may occur in situ. The plate 1 may have varying number of holes 2 for screw fixation, which may use locking or non-locking screws 5. The holes 2 may be threaded, allowing for the optional use of locking screws 5 at the discretion of the surgeon.

Figure 4:
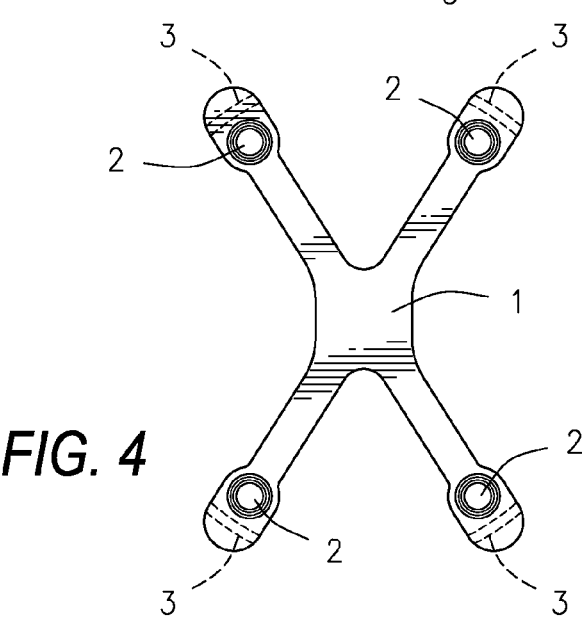
FIG. 4 is a front view of one embodiment of the plate of the bone plating system.
Figure 5:
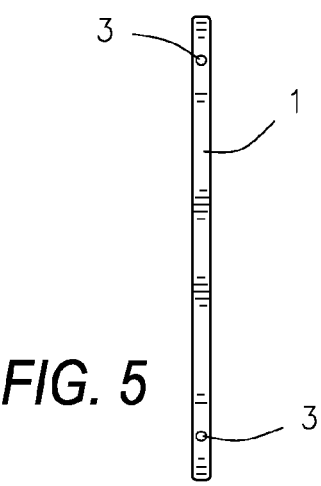
FIG. 5 is a side view of the embodiment of the plate shown in FIG. 4.
Figure 6:
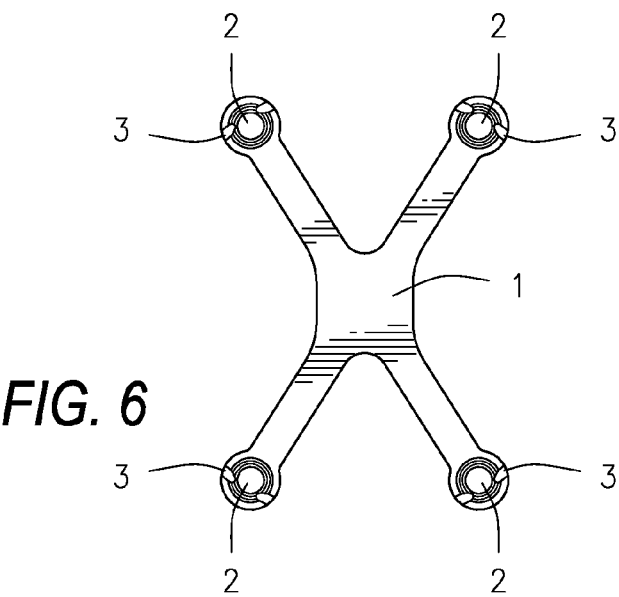
FIG. 6 is a front view of a second embodiment of the plate of the bone plating system.
Figure 7:
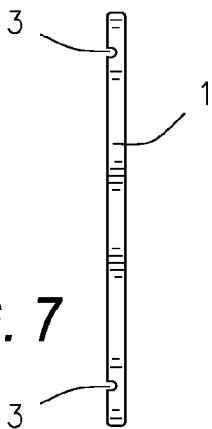
FIG. 7 is a side view of the embodiment of the plate shown in FIG. 6.

The plate 1 may have a channel or tunnel 3 at its proximal end, distal end, or both end. FIGS. 4 and 5 show a tunnel 3, while FIGS. 6 and 7 show a channel 3. A cable, suture, wire, or other flexible device 4 may run through the channel or tunnel 3. The flexible device 4 may pass through the soft tissue 11 surrounding the bone 10, such as a tendon, ligament, etc., and may secure to the plate 1. This extends fixation and neutralizes the forces of the muscles tending to pull the bone apart. If the flexible device 4 is a wire, the ends of the wire may be clamped or crimped to prevent the wire from unthreading from the channel or tunnel 3. Alternately, one end of the wire may terminate in a bead, and the other end of the wire may be clamped or crimped. If the wire ends overlap, they may be twisted together or crimped to hold the wire in place. If the flexible device 4 is a suture, it may be tied to prevent unthreading. If the channel or tunnel 3 is a channel, as shown in FIGS. 6 and 7, the channel 3 may run adjacent to the holes 2, such that the head of the screws 5 may cover the flexible device 4 and hold it in place.

All elements may be made of any suitable material. For example, the plate may be surgical stainless steel or titanium. The flexible device may be metal, elastic polymer, or any other suitable material.

In use, the surgeon begins by reducing the broken bone 10, then applying the plate 1 to the bone 10. The surgeon may contour the plate 1 in situ to allow the plate 1 to conform to the surface of the bone 10. The surgeon may then attach the plate 1 to the bone 10 with the screws 5, at least partially. Next, the surgeon passes the flexible device 4 through the channels or tunnels 3 and through the soft tissue 11 surrounding the bone 10. The surgeon then secures the flexible device 4 relative to the plate 1. If the flexible device 4 is a wire, the surgeon may twist or crimp one or both ends of the wire. If the flexible device 4 is a suture, the surgeon may tie off the suture. If the plate has channels 3 adjacent the screws 5, the surgeon may then tighten the screws 5, locking the flexible device in place within the channel 3 below the head of the screw 5. Finally, the surgeon unclamps the bone 10. The shape of the plate 1, as described below, allows the plate 1 to be applied and secured with the clamp in place on the bone 10.

Figure 1:
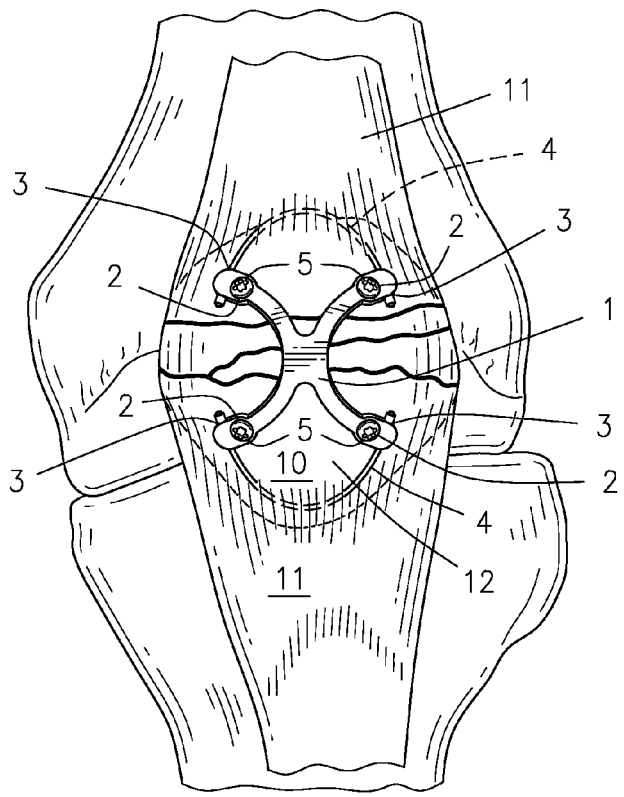
FIG. 1 is a front view of the bone plating system of the present invention in place on a patella.
Figure 2:
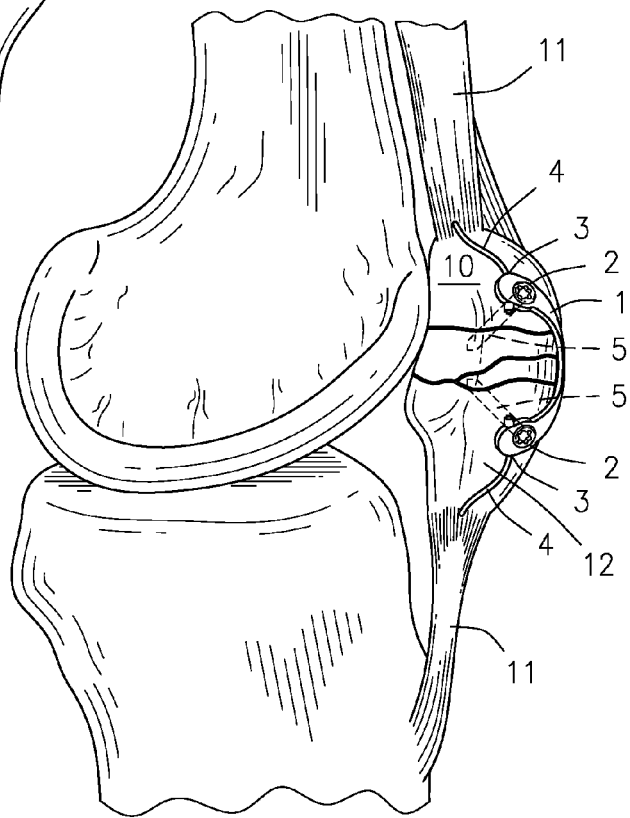
FIG. 2 is a side view of the bone plating system in place on a patella.
Figure 3:
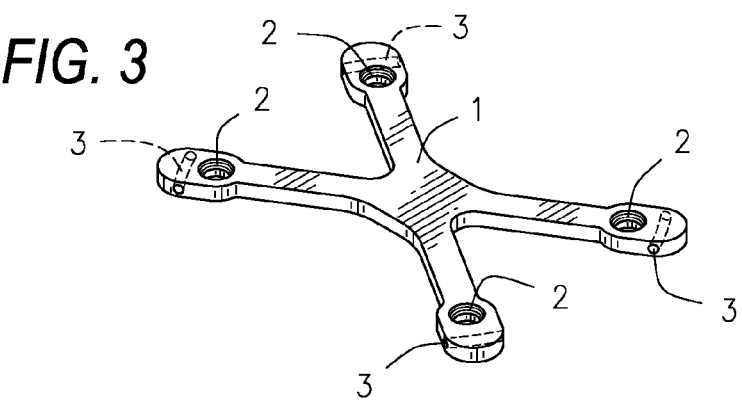
FIG. 3 is a perspective view of the plate of the bone plating system.

When used on the patella, the plate 1 may be generally X-shaped, as shown in FIGS. 1 and 2. The plate 1 may be 2 mm to 2.4 mm thick. As noted above, the plate 1 may be malleable such that it conforms to the shape of the patella 12. The plate 1 may have holes 2 at the ends of each of its four arms, into which screws 5 may be placed to secure the plate 1 to the patella 12. Channels or tunnels 3 may be located at the end of each of the four arms of the plate 1, and flexible devices 4 may run through the channels or tunnels 3 and through the soft tissue 11 surrounding the patella 12. The placement of the flexible devices 4 allows for conversion of tensile force during movement into compressive force, holding the patella 12 together.

Figure 8:
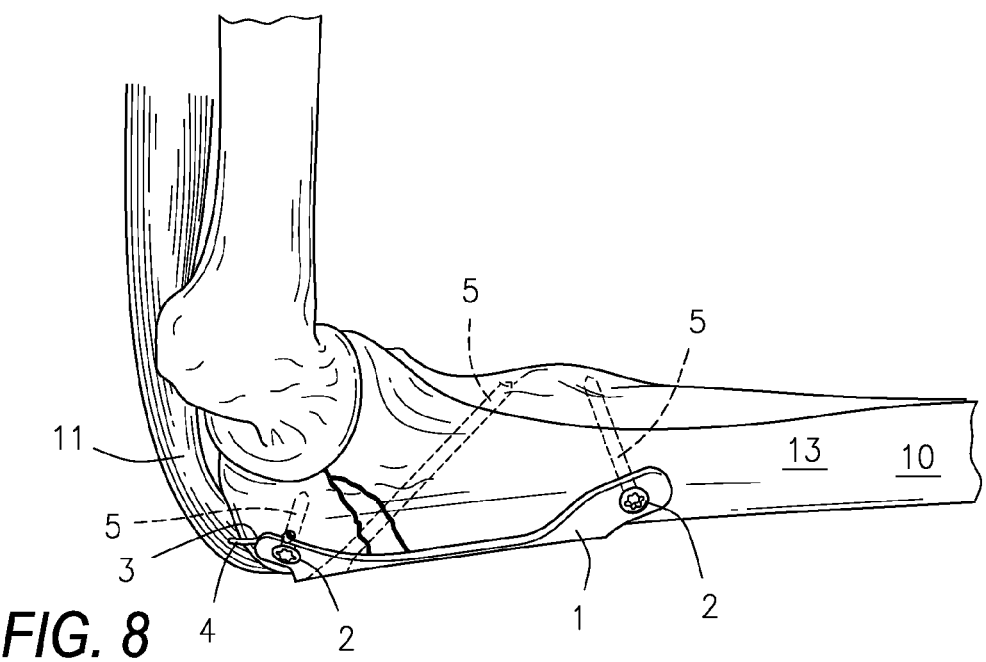
FIG. 8 is a side view of the bone plating system in place on an olecranon.
Figure 9:
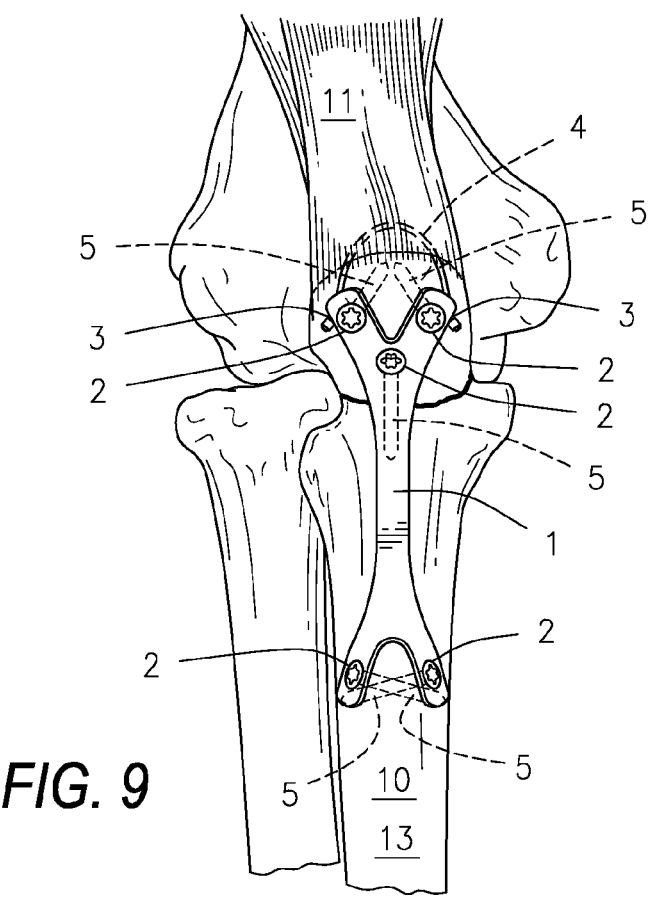
FIG. 9 is a front view of the bone plating system in place on an olecranon.

When used on the olecranon, the plate 1 may be generally long and narrow, with two arms extending from its top and two from its bottom in an elongated X shape, as seen in FIGS. 8 and 9. The plate 1 may be 2 mm to 2.4 mm thick. As noted above, the plate 1 may be malleable such that it conforms to the shape of the olecranon 13. A number of holes 2 may be located in the arms for screw fixation to the olecranon 13. Channels or tunnels 3 may run through the arms extending from the top of the plate 1, such that a flexible device 4 may pass through the channels or tunnels 3 and through the soft tissue 11 connected to and extending upward from the end of the olecranon 13.

Figures 10, 11:
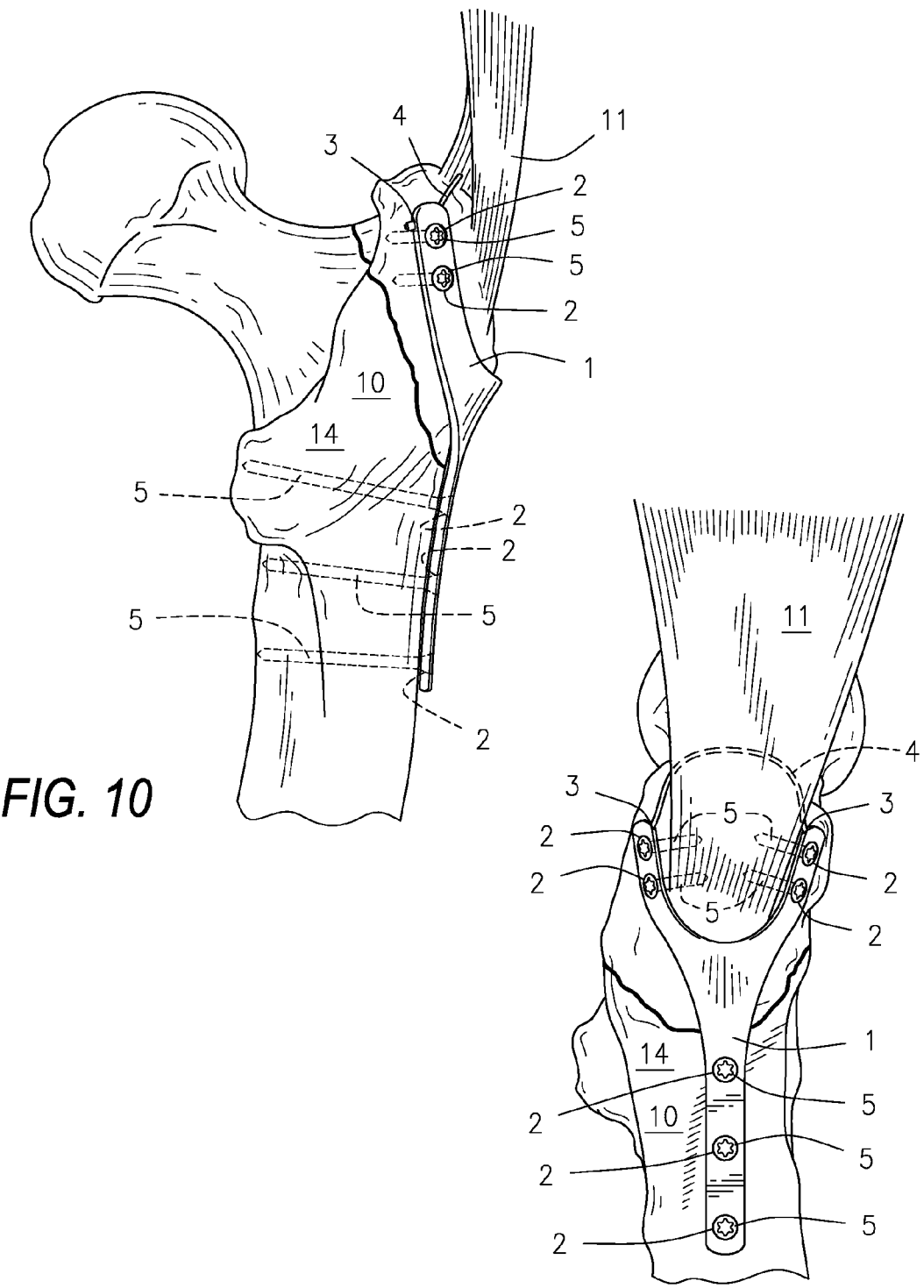
FIG. 10 is a side view of the bone plating system in place on a greater trochanter.
FIG. 11 is a front view of the bone plating system in place on a greater trochanter.

When used on the greater trochanter, the plate 1 may be generally Y-shaped, as shown in FIGS. 10 and 11. The plate 1 may be approximately 2.7 to 3.5 mm thick. As noted above, the plate 1 may be malleable such that it conforms to the shape of the greater trochanter 14. Holes 2 may be located in each of the three arms of the plate 1, allowing screws 5 to attach the plate 1 to the greater trochanter 14. Channels or tunnels 3 may be located through the upper arms of the plate 1, such that a flexible device 4 may pass through the channels or tunnels 3 and through the soft tissue 11 connected to and extending upward from the end of the greater trochanter 14.

Figure 12:
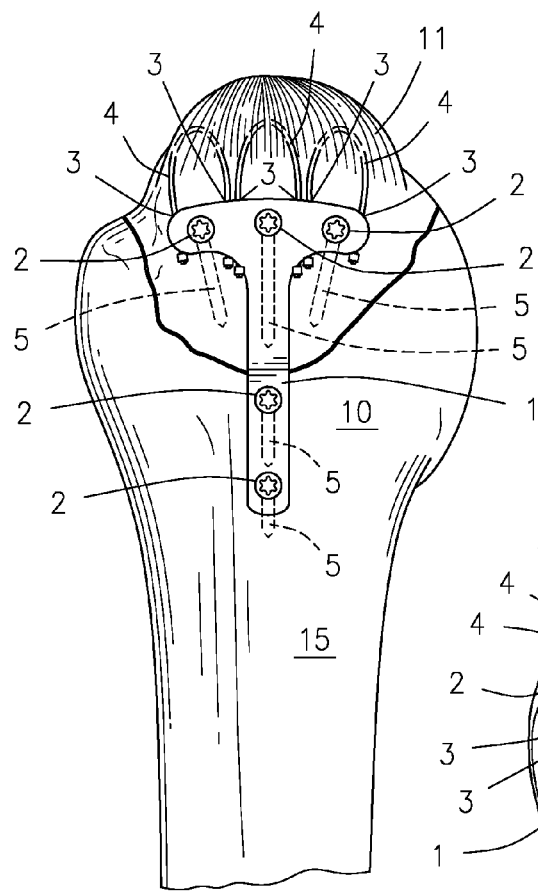
FIG. 12 is a side view of the bone plating system in place on a greater tuberosity of a humerus.
Figure 13:
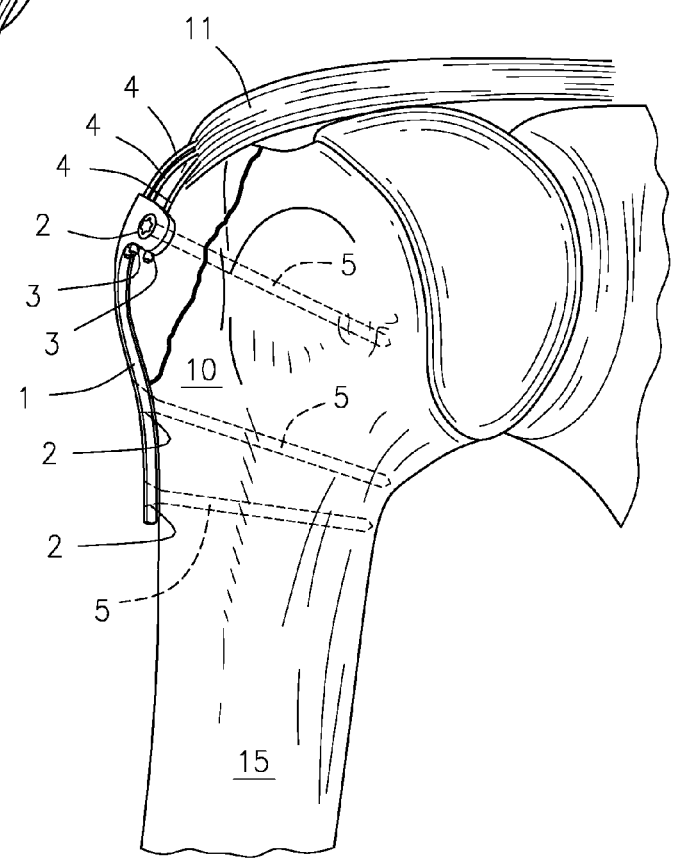
FIG. 13 is a front view of the bone plating system in place on a greater tuberosity of a humerus.

When used on the greater tuberosity, the plate 1 may be generally T-shaped, as seen in FIGS. 12 and 13. The plate 1 may be 2.4 mm to 2.7 mm thick. As noted above, the plate 1 may be malleable such that it conforms to the shape of the greater tuberosity 15. The plate 1 may have holes 2 along its downward pointing portion and along its top lateral portion, allowing screws 5 to fix the plate 1 to the greater tuberosity 15. Channels or tunnels 3 may be located in the top lateral portion of plate 1, allowing a flexible device 4 to pass through the channels or tunnels 3 and through the soft tissue 11 connected to and extending upward from the end of the greater tuberosity 15. The plate 1 may have three channels or tunnels 3, such that three loops of flexible device 4 pass through the soft tissue 11.

When used on the radial styloid, the plate 1 may be generally Y-shaped, as shown in FIGS. 14 and 15, with holes 2 located throughout the plate 1, allowing screws 5 to fix the plate 1 to the radial styloid 16. The plate 1 may be 2 mm thick. As noted above, the plate 1 may be malleable such that it conforms to the shape of the radial styloid 16. Channels or tunnels 3 may be located in the top branches of the plate 1, such that a flexible device 4 may pass therethrough and through the soft tissue 11 attached to and extending from the radial styloid 16.

Figure 16:
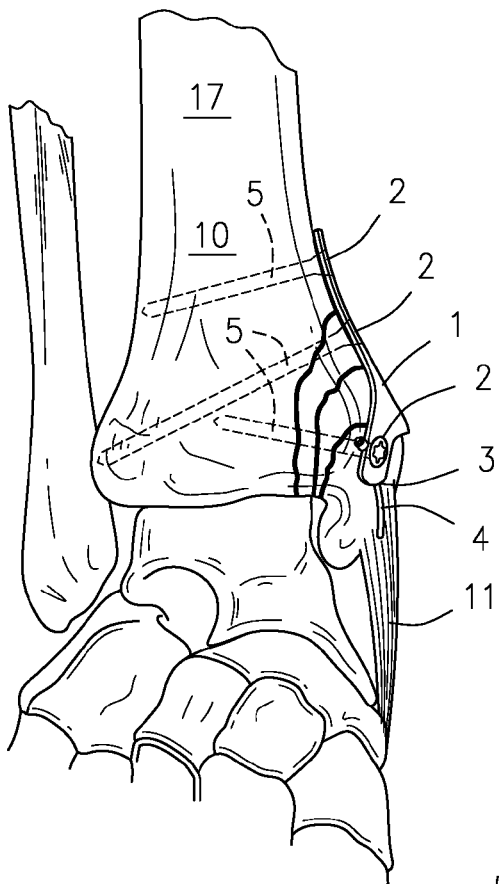
FIG. 16 is a side view of the bone plating system in place on a medial malleoli.
Figure 17:
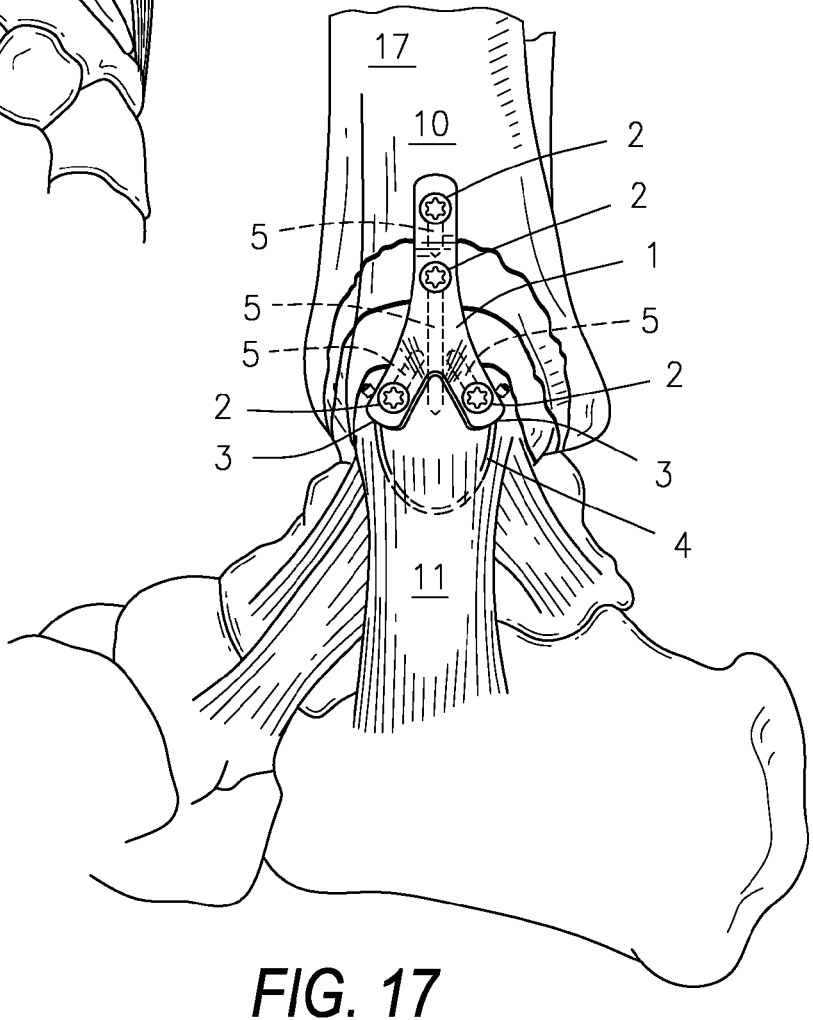
FIG. 17 is a front view of the bone plating system in place on a medial malleoli.

When used on the medial malleoli, as seen in FIGS. 16 and 17, the plate 1 may be generally Y-shaped with holes 2 located throughout. Oriented on the body, the Y-shaped plate 1 may be generally oriented downward, as an upside-down Y. The plate 1 may be 2 mm to 2.4 mm thick. As noted above, the plate 1 may be malleable such that it conforms to the shape of the medial malleoli 17. Screws 5 may attach the plate 1 to the medial malleoli 17. Channels or tunnels 3 may be located in the downward extending branches of the plate 1, such that flexible device 4 passing therethrough may pass through the soft tissue 11 attached to and extending downward from the medial malleoli 17.

Figure 18:
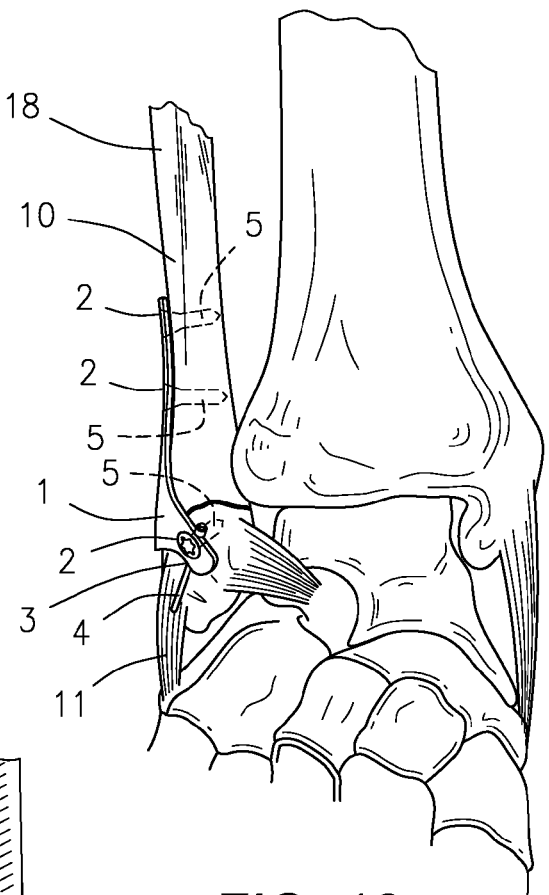
FIG. 18 is a side view of the bone plating system in place on a lateral malleolus of a fibula.
Figure 19:
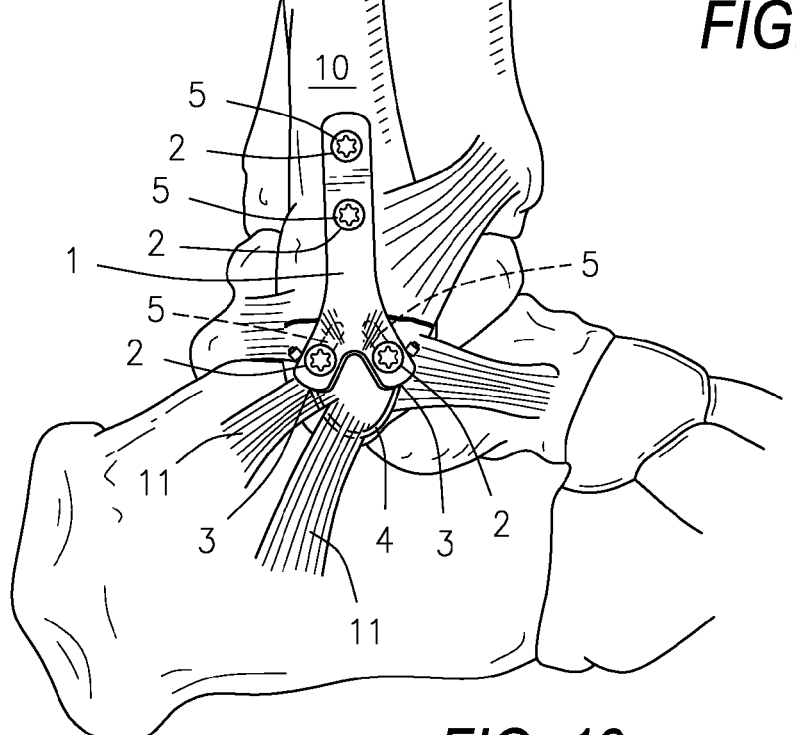
FIG. 19 is a front view of the bone plating system in place on a lateral malleolus of a fibula.

When used on the fibula, the plate may likewise be generally upside-down Y-shaped, as seen in FIGS. 18 and 19. The plate 1 may be 2 mm to 2.4 mm thick. As noted above, the plate 1 may be malleable such that it conforms to the shape of the fibula 18. Holes 2 throughout the plate 1 may allow the plate 1 to be attached to the fibula 18 via screws 5. Channels or tunnels 3 may be located in the downward extending branches of plate 1, such that a flexible device may pass through the channels or tunnels 3 and through the soft tissue 11 attached to and extending downward from the fibula 18.

The plates 1 may be designed to function (biomechanically) purely as tension bands. Because of the small size, low profile, and ductility of the plates 1, they may play a unique role in treating simple periarticular fractures that require both fracture compression and neutralization of soft tissue distracting forces. The cabling or suture component 4 associated with these plates 1 extends surgical fixation of the implant construct by having an attached cable, suture, wire, or other flexible device 4 that is passed into the surrounding soft tissues 11 and then secured to the plate 1. This technique may neutralize tensile deforming forces acting across the fixation construct.

The system is designed to augment and extend fixation. A cable wire, suture, or other flexible device 4 may pass through the surrounding soft tissue 11 to extend fixation when small fragments or limited bone is available for screw fixation. The low profile design of plate 1 may better accommodate small bone fracture location due to limited soft tissue coverage. The plate 1 may have a limited bone footprint that diminishes potential devascularization of the healthy bone. The low profile plate 1 may allow for easier placement without the removal of the reduction clamp. This is a significant benefit to the tension band plating system.

The low profile plate 1 with flexible device 4 may be used in prominent bony areas with limited tissue coverage where current fracture plates are too bulky. This technique replaces the figure eight tension band wire currently used, which is difficult to place, remains prominent, and applies a variable and unknown amount of tension. The current plates 1 are designed exclusively to function as a tension band and therefore able to be much smaller and lower profile than traditional periarticular plating systems. Traditional plates are currently too bulky and cumbersome to implant. Traditional cable fixation encircles the bone and induces a variable but often large amount of soft tissue trauma, potentially devitalizing the surrounding bone. The flexible device 4 of the present invention typically does not encircle the bone, which results in less soft tissue damage and therefore less bone devitalization.

Whereas, the devices and methods have been described in relation to the drawings and claims, it should be understood that other and further modifications, apart from those shown or suggested herein, may be made within the spirit and scope of this invention.

What is claimed is:

1. A bone plating system comprising:
   a plate, where the plate is low-profile and capable of contouring to a bone;
   at least one channel or tunnel through the plate;
   at least one flexible device passing through the channel or tunnel and capable of
   passing through soft tissue attached to the bone, where the at least one flexible device does not surround the bone;
   the bone is a patella;
   soft tissue extends upward from the patella and downward from the patella or encircles the patella;
   the plate is generally X-shaped, such that the plate has two arms extending generally upward and two arms extending generally downward;
   the at least one channel or tunnel passes through each of the two arms extending generally upward from the plate and each of the two arms extending generally downward from the plate;
   the flexible device passes through the channel or tunnel in each of the two arms extending generally upward such that the flexible device is capable of passing through the soft tissue extending upward from the patella; and
   a second flexible device passes through the channel or tunnel in each of the two arms extending generally downward such that the flexible device is capable of passing through the soft tissue extending downward from the patella.

2. The bone plating system of claim 1 where the at least one flexible device is capable of neutralizing tensile forces.

3. The bone plating system of claim 1 where the plate is capable of being contoured to the bone in situ.

4. The bone plating system of claim 1, further comprising one or more holes in the plate and one or more screws attaching the plate to the bone via the one or more holes.

5. The bone plating system of claim 4 where the one or more holes are threaded and the one or more screws are locking screws, non-locking screws, or a combination thereof.

6. The bone plating system of claim 1 where the at least one flexible device is a cable, suture, wire, elastic polymer, or combination thereof.

7. The bone plating system of claim 1 where the soft tissue is a tendon, ligament, or fascia.

* * * * *